United States Patent [19]
Fox et al.

[11] Patent Number: 6,031,124
[45] Date of Patent: Feb. 29, 2000

[54] 7-AMINO-2-HEPTENOATES AND THEIR USE IN THE PREPARATION OF METHYLPHENIDATE

[75] Inventors: Martin Edward Fox; Jane Marie Paul, both of Cambridge, United Kingdom

[73] Assignee: Medeva Europe Limited, United Kingdom

[21] Appl. No.: 09/155,322

[22] PCT Filed: Mar. 21, 1997

[86] PCT No.: PCT/GB97/00811

§ 371 Date: Sep. 25, 1998

§ 102(e) Date: Sep. 25, 1998

[87] PCT Pub. No.: WO97/35836

PCT Pub. Date: Oct. 2, 1997

[30] Foreign Application Priority Data

Mar. 27, 1996 [GB] United Kingdom .................... 9606417

[51] Int. Cl.$^7$ .................................................. C07C 229/00
[52] U.S. Cl. .............................. 560/37; 558/390; 560/27; 564/164
[58] Field of Search ............................... 558/390; 560/37, 560/27; 564/164

[56] References Cited

U.S. PATENT DOCUMENTS 2,957,880  10/1960  Rometsch ................................. 546/233

FOREIGN PATENT DOCUMENTS 53-007627  1/1978  Japan .

OTHER PUBLICATIONS

Knouzi, N. et al. (1987) Intramolecular Cyclization of ω–Primary Amino Electrophilic Olefins to Functionalized Pyrrolidines and Piperidines. Tetrahedron Letters 28(16): 1757–1760.

*Primary Examiner*—Paul J. Killos
*Assistant Examiner*—Taylor V. Oh
*Attorney, Agent, or Firm*—Saliwanchik, Lloyd & Saliwanchik

[57] ABSTRACT

The subject invention pertains to compounds of the formula $Y^1Y^2N-(CH_2)_4-CH=C(Ph)-X$ wherein $Y^1$ and $Y^2$ are independently H or a removable blocking group, or $Y^1$ and $Y^2$ together are a removable divalent blocking group; and X is $COOCH_3$ or a group convertible thereto. Such a compound may be cyclised, by Michael addition, to give methylphenidate, if necessary after removing blocking group(s) and converting X to $COOCH_3$. The subject invention also pertains to methods for preparing compounds of the invention.

15 Claims, No Drawings

7-AMINO-2-HEPTENOATES AND THEIR USE IN THE PREPARATION OF METHYLPHENIDATE

FIELD OF THE INVENTION

This invention relates to the synthesis of methylphenidate by cyclisation of new 7-amino-2-heptenoates.

BACKGROUND OF THE INVENTION

Methylphenidate has utility as a therapeutic agent, e.g. in the treatment of attention-deficient hyperactivity disorder. It was first prepared as a mixture of the erythro and threo racemates. U.S. Pat. No. 2,957,880 discloses its synthesis and also studies upon the two racemic mixtures, which revealed that the therapeutic activity resides in the threo diastereomer.

JP-A-53007627 discloses the formula

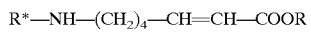

wherein R* is the chiral auxiliary α-methylbenzylamine and R is lower alkyl. This structure is indicated as suitable for cyclisation to 1-(1-phenylethyl)-2-hydroxy-5-piperidinone, en route to antihistaminic agents.

No cyclisation is demonstrated. Further, the elemental analysis of the compound that is made, consistent with the intended product, indicates that it is actually of the formula

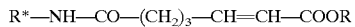

The fact that this is an amide may account for failure of the proposed cyclisation.

Knouzi et al, Tet. Lett. 28(16):1757–60 (1987), disclose cyclisation, again by Michael addition, of 7-arnino-2-heptenoates of the formula

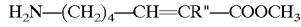

wherein R" is H or $CH_3$. The resultant piperidines, and also analogous compounds, were obtained with good diastereoselectivity, except for the given compound when R" is $CH_3$.

SUMMARY OF THE INVENTION

The present invention is based on the realisation that compounds of formula I $$Y^1Y^2N-(CH_2)_4-CH=CPh-X \qquad (I)$$

wherein $Y^1$ and $Y^2$ are independently H or a removable blocking group, or $Y^1$ and $Y^2$ together are a removable divalent blocking group, and X is $COOCH_3$ or a group convertible thereto, are novel intermediates that provide the basis of a new synthesis of methylphenidate. Further, cyclisation by Michael addition proceeds substantially only on one of the two geometric isomers. Thus, contrary to the most closely analogous situation in the prior art, effective and useful diastereoselectivity is found.

Therefore, according to a further aspect of this invention, compounds of formula I when $Y^2$ is H can be converted to methyiphenidate by Michael addition, using a base such as lithium diethylamine, removing any blocking group represented by $Y^1$, and converting X to $COOCH_3$, if necessary.

According to yet another aspect of the invention, compounds of formula I may be prepared by a Horner-Wadsworth-Emmons reaction of corresponding compounds of the formulae 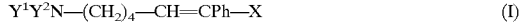 and $Y^1Y^2N-(CH_2)_4-CHO$, wherein $Y^2$ is a blocking group; and, if desired, removing the blocking group to give the product in which $Y^2$ is H.

DESCRIPTION OF THE INVENTION

X is preferably $COOCH_3$. Alternatively, it may be CN, $CONH_2$ or $COOR^1$, $R^1$ being H or alkyl or aralkyl of up to 10 C atoms. Other groups X that can readily be converted to $COOCH_3$, and methods of conversion, will be readily apparent to one of ordinary skill in the art.

$Y^1$ and $Y^2$ may each be H. Either or each, or the two together, may also be a blocking group. Groups that can readily be introduced onto a N atom, and readily removed after another part of the molecule has undergone reaction, are well known to those of ordinary skill in the art. For example, reference may be made to T. W. Greene et al, "Protecting Groups in Organic Synthesis", 2nd ed. Wiley-Interscience, New York (1991). A particular example of a suitable blocking group is t-butyloxycarbonyl (Boc). An example of $Y^1$ and $Y^2$ together with N is phthalimido.

In certain circumstances, it may be preferred that $Y^1$ is a chiral auxiliary, in single enantiomer form. A preferred example is 1-phenylethyl, which may be introduced using, say, α-methylbenzylaiine (α-MBA), and removed by hydrogenation. The use of a chiral auxiliary may assist control of absolute and/or relative stereochemistry. Either enantiomer may be used, depending on the desired product, and this may readily be determined by experiment. Any erythro diastereoisomer formed by cyclisation may be subjected to epimerisation at the benzylic position to give optically-enriched threo methylphenidate or a derivative thereof.

Each of the reactions described herein may be conducted by generally known methodology, and any variations that may be necessary for optimisation can readily be determined by one of ordinary skill in the art. Any desired resolution, e.g. to obtain d-threo-methylphenidate, may be conducted by known means. Preferred resolution processes are described in PCT/GB97/00185 and PCT/GB97/00643. Such resolutions may be combined with the racemisation described in PCT/GB97/00281. The contents of these copending Applications are incorporated herein by reference.

Scheme 1 illustrates a synthesis of a racemic compound of formula I. Scheme 2 illustrates a synthesis of optically pure compound of formula I, starting from glutaric anhydride and optically-pure α-MBA. The four steps of Scheme 1 are further illustrated by the following Examples 1 to 4, respectively. Example 5 illustrates the cyclisation by Michael addition.

EXAMPLE 1

5-Amino-1-pentanol (30.0 g, 0.29 mol) and acetophenone (34.9 g, 0.29 mol) were condensed by refluxing in toluene (100 ml) under Dean and Stark conditions in the presence of 1% $ZnCl_2$ (20 mg). Toluene was removed and substituted with MeOH (100 ml), and then $NaBH_4$ (10.8 g, 0.29 mol) was added to reduce the imine. MeOH was removed and the product was partitioned between EtOAc (150 ml) and water (150 ml). After aqueous workup, the amine was obtained as a yellow oil (51 g, 85%).

EXAMPLE 2

The secondary amine was protected by a Boc group. The amine (38.0 g, 18 mol) was treated with 1 eq $Boc_2O$ (39.9 g, 0.18 mol) in a biphasic mixture of THF/2M NaOH (200 ml) for 2 hrs. The product was chromatographed on silica using EtOAc/heptane 1:1 to afford the Boc-protected amide (50.0 g, 89%).

EXAMPLE 3

The alcohol (17.0 g, 0.55 mol) was oxidised to the aldehyde using standard conditions (DMSO-oxalyl chloride-TEA) (3:1.5:7 in DCM). The crude product was chromatographed through silica with EtOAc/heptane 2:8, to afford the aldehyde as a yellow oil (11.52 g, 68%).

EXAMPLE 4

Methyl (+)-2-bromophenylacetate (51.14 g, 96%) was prepared from the free acid (50.0 g, 0.23 mol) in 96% yield with 1 eq of acetyl chloride (18.3 g, 16.5 ml) in methanol (20 ml) at room temperature. Triethyl phosphite (12.35 ml, 0.72 mol) was added over a period of 20 minutes to methyl α-bromophenyl acetate (15.0 g, 0.65 mol) at 120° C., and then the mixture was heated for 3 hrs at 160° C. The phosphonate was isolated cleanly in quantitative yield (19.5 g, 100%).

1 M (Me$_3$Si)NNa (4.9 ml) was added to a solution of the phosphonate (1.4 g, 4.91 mmol) in THF (5 ml) at −78° C. A solution of the aldehyde (1.0 g, 3.27 mmol) in THF (5 ml) was added dropwise. The solution was warmed to room temperature overnight. After aqueous workup, a 1:1 mixture of the geometric isomers of formula I was obtained (0.89 g; 66%).

Treatment of the Boc-protected amino-alkene (0.89 g, 2.0 mmol) with neat TFA (2 ml) cleanly removed the Boc group. The trifluoroacetate salt was treated with TEA (2 ml) in MTBE (5 ml). Surprisingly, the free amine was isolated rather than the cyclised product (0.69 g; 101%).

EXAMPLE 5

A dilute solution of the free amine (0.66 g, 1.98 mmol) in THF (10 ml) was added dropwise to freshly prepared 0.28 MLDA (8.5 ml, 2.38 mmol) in THF (50 ml) at −78° C. The mixture was then warmed to −20° C. over 2 h, before being quenched with saturated ammonium chloride.

The $^1$H NMR spectrum of the crude product showed that one geometric isomer of the starting material had not reacted while the other isomer had undergone a Michael addition. Column chromatography of the product mixture gave a single geometric isomer of unreacted amine and the cyclised product.

The sample of cyclised material is not completely pure, but the $^1$H NMR spectrum indicates that 2:1 mixture of major diastereomers has been produced. In theory, four diastereomers could be produced in this reaction, therefore there is good diastereoselectivity.

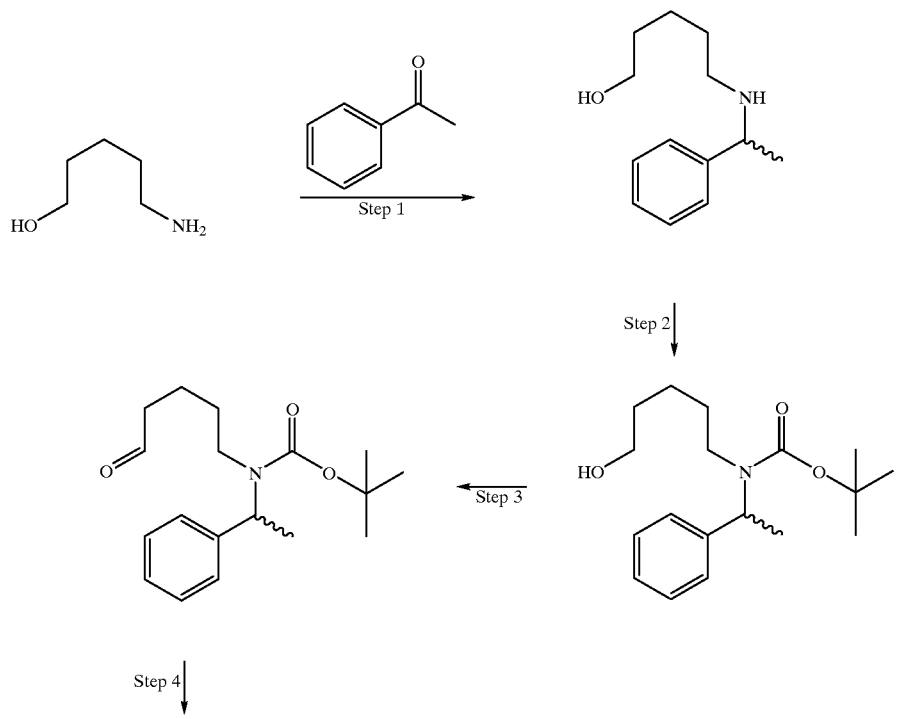

Scheme 1

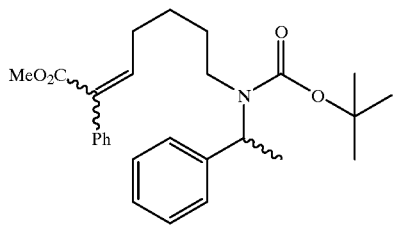

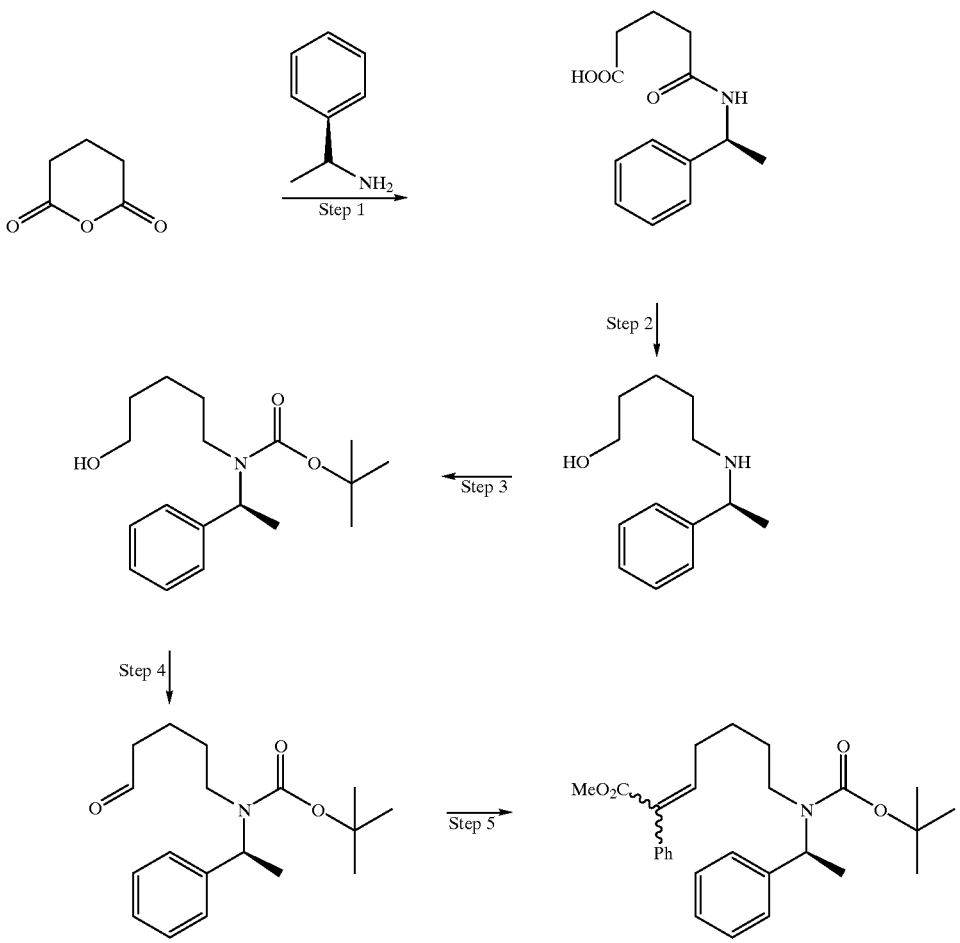

We claim:

1. A compound of the formula

Y¹Y²N—(CH₂)₄—CH=C(Ph)—X wherein $Y^1$ and $Y^2$ are independently H or a removable blocking group, or $Y^1$ and $Y^2$ together are a removable divalent blocking group; and X is COOCH₃ or a group that can be converted to COOCH₃.

2. The compound according to claim 1, wherein X is CN, CONH₂ or COOR¹, R¹ being H or alkyl or aralkyl of up to 10 C atoms.

3. The compound according to claim 1, wherein $Y^1$ is H or a chiral auxiliary.

4. The compound according to claim 1, wherein $Y^1$ is 1-phenylethyl.

5. The compound according to claim 3, wherein $Y^2$ is H.

6. A process for preparing a compound of claim 1, which comprises a Horner-Wadsworth-Emmons reaction of corresponding compounds of the formulae Ph—CHX—PO(Oalk)₂ and Y¹Y²N—(CH₂)₄—CHO, wherein $Y^2$ is a blocking group.

7. A process for preparing methylphenidate, which comprises a Michael reaction, using base, on a compound according to claim 5; removing any blocking group represented by $Y^1$; and, if X is not COOCH₃, converting it to COOCH₃.

8. The process according to claim 7, wherein the base is lithium diethylamine.

9. The process according to claim 7, wherein $Y^1$ is 1-phenylethyl and it is removed by hydrogenation.

10. The process according to claim 6, further comprising removing the blocking group to give the product in which $Y^2$ is H.

11. The compound according to claim 2, wherein $Y^1$ is H or a chiral auxiliary.

12. The compound according to claim 4, wherein $Y^2$ is H.

13. The process according to claim 8, wherein $Y^1$ is 1-phenylethyl and it is removed by hydrogenation.

14. The compound according to claim 2, wherein $Y^1$ is 1-phenylethyl.

15. The compound according to claim 3, wherein $Y^1$ is 1-phenylethyl.

* * * * *

UNITED STATES PATENT AND TRADEMARK OFFICE
CERTIFICATE OF CORRECTION

PATENT NO. : 6,031,124
DATED : February 29, 2000
INVENTOR(S) : Martin Edward Fox, Jane Marie Paul It is certified that error appears in the above-indentified patent and that said Letters Patent is hereby corrected as shown below:

Column 6, line 59: "Homer-Wadsworth-Emmons" should read
--Horner-Wadsworth-Emmons--.

Signed and Sealed this

Third Day of April, 2001

Attest:

NICHOLAS P. GODICI

*Attesting Officer*  Acting Director of the United States Patent and Trademark Office